(12) United States Patent
Itoh

(10) Patent No.: US 7,578,383 B2
(45) Date of Patent: Aug. 25, 2009

(54) SPECIMEN TRANSPORT SYSTEM

(75) Inventor: Teruaki Itoh, Kumamoto (JP)

(73) Assignee: IDS Co., Ltd., Kumamoto (JP)

( * ) Notice: Subject to any disclaimer, the term of this patent is extended or adjusted under 35 U.S.C. 154(b) by 52 days.

(21) Appl. No.: 11/892,598

(22) Filed: Aug. 24, 2007

(65) Prior Publication Data
US 2008/0053790 A1 Mar. 6, 2008

(30) Foreign Application Priority Data
Aug. 31, 2006 (JP) ............... 2006-236940

(51) Int. Cl.
*B65G 47/34* (2006.01)
(52) U.S. Cl. .............. 198/468.9; 198/468.01; 414/222.08; 414/331.06
(58) Field of Classification Search .............. 198/468.9, 198/468.6, 468.01, 347.1; 414/222.08, 222.09, 414/331.06, 332
See application file for complete search history.

(56) References Cited
U.S. PATENT DOCUMENTS

| | | | |
|---|---|---|---|
| 5,069,598 A * | 12/1991 | Kleinhen et al. | 198/468.9 |
| 5,525,025 A * | 6/1996 | Ootmar Ten Cate et al. | 414/222.08 |
| 6,301,776 B1 * | 10/2001 | Myung et al. | 198/468.9 |
| 7,304,260 B2 * | 12/2007 | Boller et al. | 198/468.9 |
| 7,311,487 B1 * | 12/2007 | Crossley et al. | 414/331.06 |

FOREIGN PATENT DOCUMENTS

JP 2005-300357 10/2005

* cited by examiner

*Primary Examiner*—James R Bidwell
(74) *Attorney, Agent, or Firm*—Nixon & Vanderhye P.C.

(57) ABSTRACT

A specimen transport system for transporting a specimen, includes, a preceding section, a succeeding section located apart from the preceding section, a conveyor-type rack transport mechanism attached to the preceding section and/or the succeeding section and configured to transport a rack capable of holding a plurality of specimen containers which contain the specimen, and a car configured to travel between the preceding section and the succeeding section and provided with a conveyor-type rack transport mechanism configured to transport the rack capable of holding a plurality of specimen containers which contain the specimen.

6 Claims, 11 Drawing Sheets

SPECIMEN TRANSPORT SYSTEM

CROSS-REFERENCE TO RELATED APPLICATIONS

This application is based upon and claims the benefit of priority from prior Japanese Patent Application No. 2006-236940, filed Aug. 31, 2006, the entire contents of which are incorporated herein by reference.

BACKGROUND OF THE INVENTION

1. Field of the Invention

The present invention relates to a specimen transport system for transporting a specimen by means of a car.

2. Description of the Related Art

A specimen transport system is a known technique in which a specimen, e.g., blood, in containers such as test tubes is transported by means of a car configured to travel between a preceding section and a succeeding section that are spaced apart from each other. This technique obviates the necessity of a transport mechanism that is dedicated to the movement of the specimen. As described in Jpn. Pat. Appln. KOKAI Publication No. 2005-300357, for example, one such specimen transport system is designed so that the specimen is moved between the car and each section by using a transfer device.

The preceding section comprises a holder transport mechanism for transporting the specimen containers for each specimen holder, on the upstream side with respect to its transport direction, and a rack transport mechanism for transporting the specimen containers for each rack that contains a plurality of specimen containers, on the downstream side with respect to the transport direction. Further, the preceding section comprises a container hand transfer device that transfers the specimen containers in the holder transport mechanism to racks of the rack transport mechanism. Furthermore, the preceding section comprises a rack transfer device that lifts the racks from the rack transport mechanism and sets them onto a rack transport mechanism on the car. The succeeding section comprises a rack transport mechanism for transporting the specimen containers for each rack, on the upstream side with respect to its transport direction, and a holder transport mechanism for transporting the specimen containers for each holder, on the downstream side with respect to the transport direction. Further, the succeeding section comprises a rack transfer device that lifts the racks set on the rack transport mechanism on the car and sets them onto its succeeding rack transport mechanism. Furthermore, the succeeding section comprises a container hand transfer device that successively draws out the specimen containers, a predetermined number at a time, from the racks on the rack transport mechanism and transfers them to the holder transport mechanism. This rack transfer device moves the racks from the preceding section to the car and from the car to the succeeding section.

Since the specimen transport system described above uses the rack transfer device for rack movement, however, the configurations of its components are complicated. Further, operation for rack movement such as to lift and move the racks one after another by the rack transfer device is complicated and time-consuming.

Accordingly, an object of the present invention is to provide a specimen transport system of a simple configuration in which operation for moving racks between a car and a preceding or succeeding section can be simplified to ensure shorter operating time.

BRIEF SUMMARY OF THE INVENTION

An aspect of the invention is; a specimen transport system for transporting a specimen, comprising; a preceding section, a succeeding section located apart from the preceding section, a conveyor-type rack transport mechanism attached to the preceding section and/or the succeeding section and configured to transport a rack capable of holding a plurality of specimen containers which contain the specimen, and a car configured to travel between the preceding section and the succeeding section and provided with a conveyor-type rack transport mechanism configured to transport the rack capable of holding a plurality of specimen containers which contain the specimen.

An aspect of the invention is a car for specimen transport comprising; wheels, a redirection mechanism configured to redirect the wheels at right angles, and a conveyor-type rack transport mechanism configured to transport a rack capable of holding a plurality of specimen containers which contain a specimen, and configured to travel between a preceding section and a succeeding section which are spaced apart from each other.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
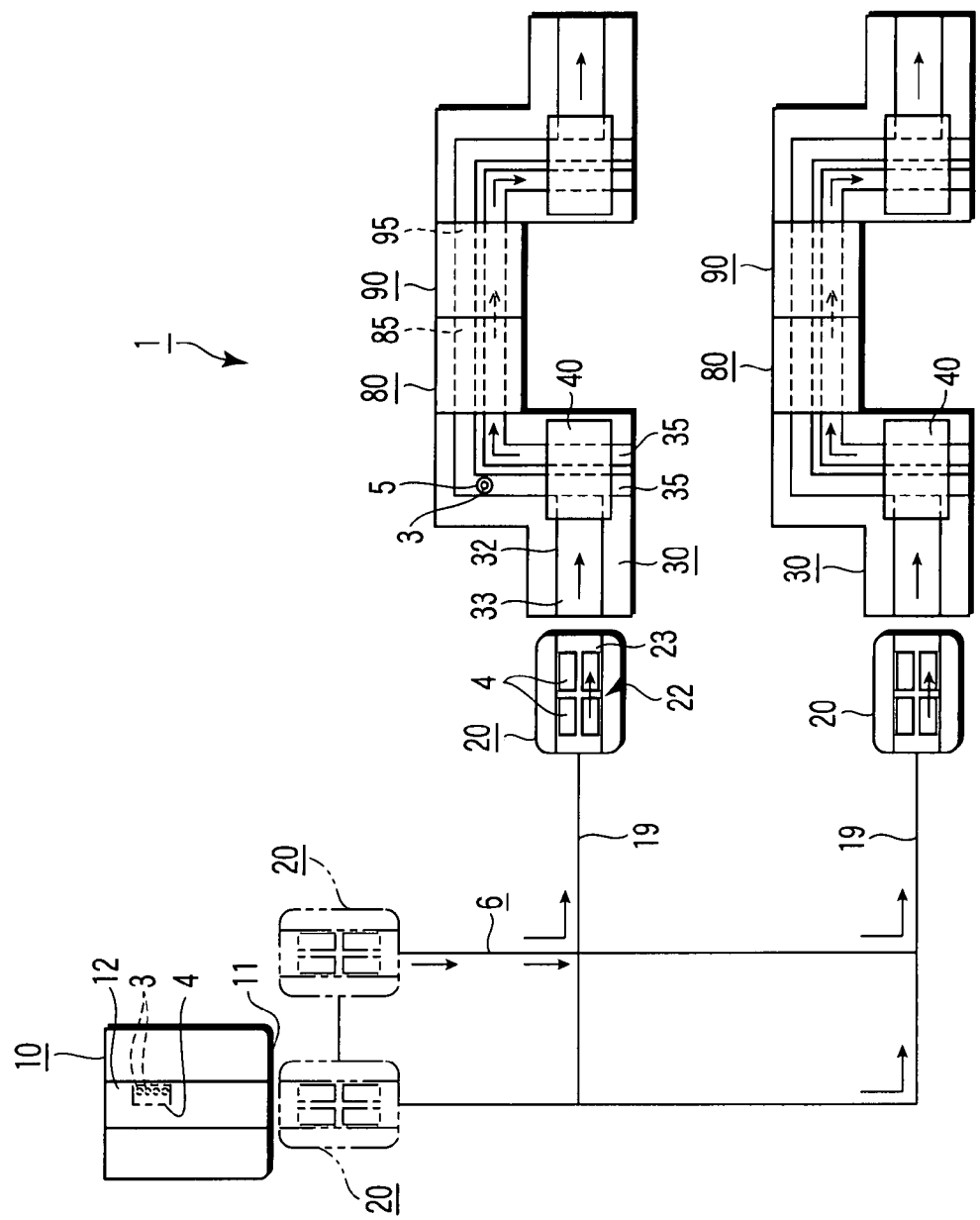
FIG. 1 is a plan view schematically showing a specimen transport system according to a first embodiment of the invention.
Figure 2:
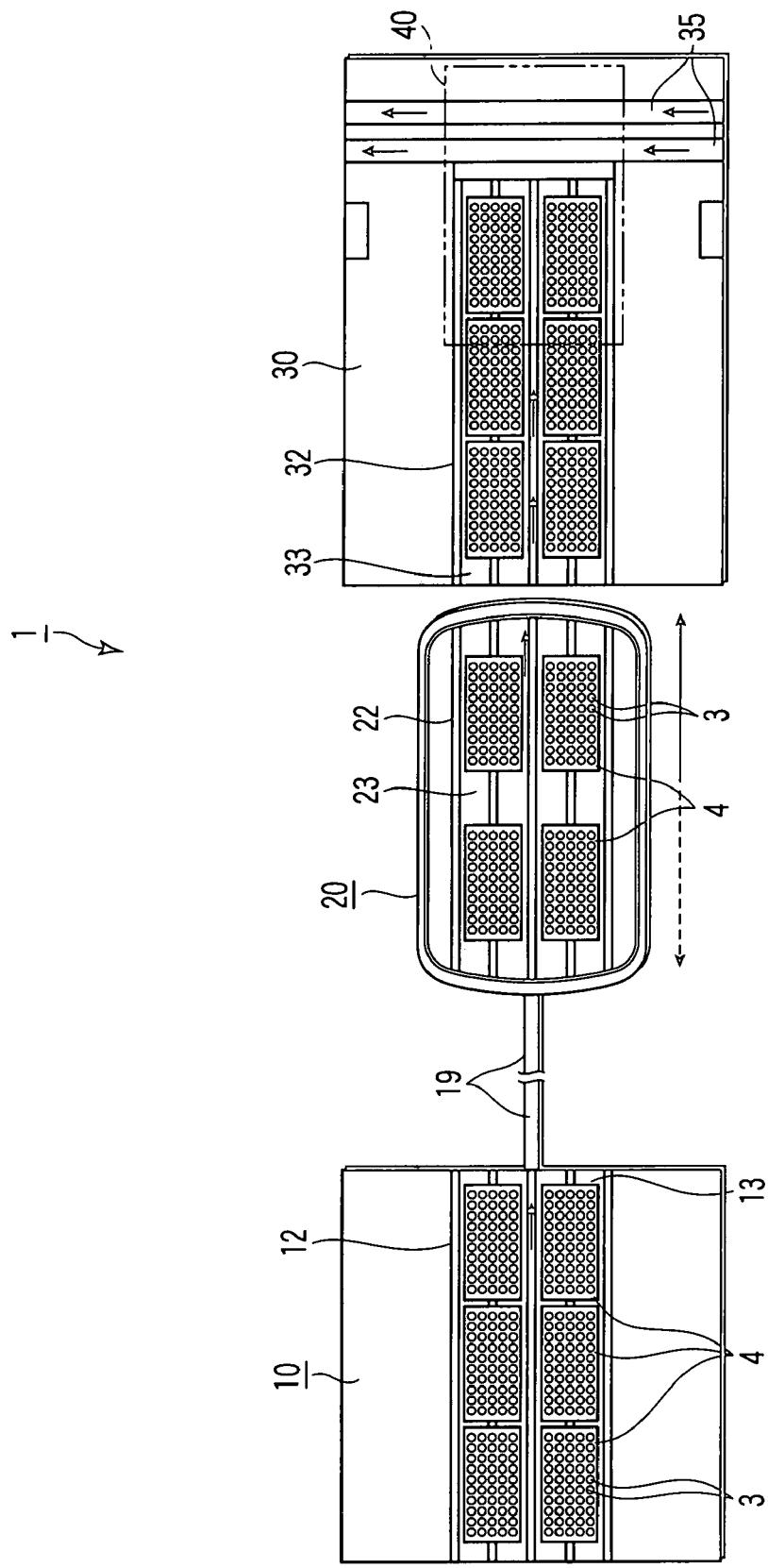
FIG. 2 is a plan view schematically showing a part of the specimen transport system of FIG. 1.
Figure 3:
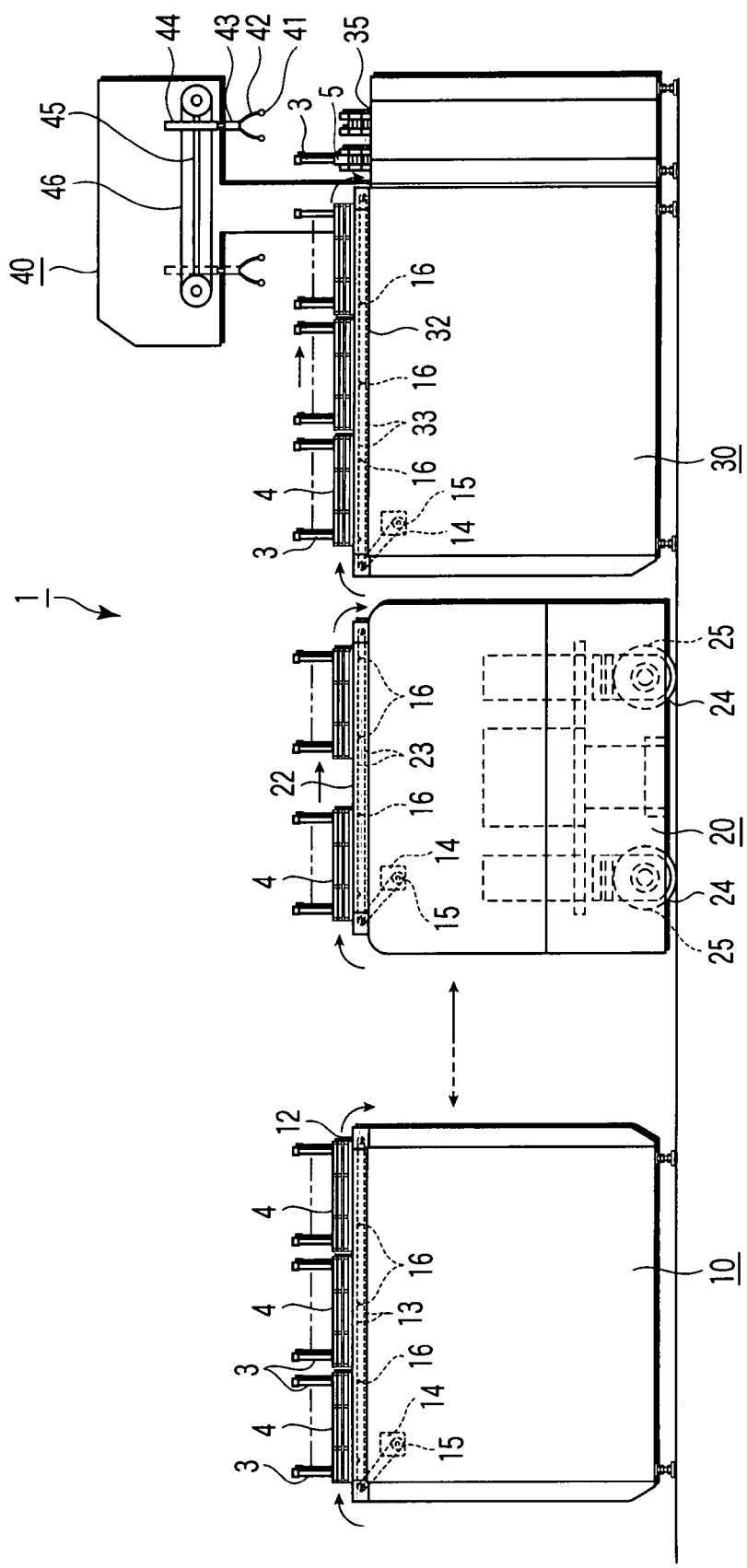
FIG. 3 is a side view schematically showing a part of the specimen transport system.

The following is a description of a specimen transport system 1 according to a first embodiment of the present invention. FIG. 1 is a schematic plan view of the system 1 of the present embodiment. FIGS. 2 and 3 are schematic plan and side views, respectively, showing a part of the system 1. In each of these drawings, solid-line arrows indicate a transport direction, while broken-line arrows indicate a direction reverse to the transport direction. For ease of illustration, some configurations are shown in an enlarged or contracted manner or not shown in the drawings.

The specimen transport system 1 serves to transport specimen containers 3, which contain a specimen 2 such as blood, for each rack 4 or each specimen holder 5 in the arrowed transport direction along a transport line 6. The transport line 6 threads through specimen processing units 10 and 30 for variously processing the specimen, etc. The specimen transport system 1 comprises specimen processing units 10, 30, 80 and 90, including a preceding unit 10 as a preceding section and a succeeding unit 30 as a succeeding section, and a car 20 that can reciprocate in the transport direction and the direction reverse thereto along a guide 19 located between the processing units.

The preceding unit 10, car 20, and succeeding unit 30 are provided with a conveyor-type preceding rack transport mechanism 12, a car rack transport mechanism 22, and a succeeding rack transport mechanism 32, respectively. The preceding rack transport mechanism 12 transports each rack 4 that can contain a plurality of specimen containers 3. Further, the succeeding unit 30 and the other specimen processing units 80 and 90 are provided, respectively, with succeeding holder transport mechanisms 35, 85 and 95 that can transport the specimen containers 3 for each specimen holder 5. By feed motions of the transport mechanisms 12, 22, 32, 35, 85 and 95 and traveling motion of the car 20, the specimen containers 3 are transported for each rack 4 or each specimen holder 5, covering the entire transport line 6 that is composed of the transport mechanisms 12, 22, 32, 35, 85 and 95 and the guide 19.

The preceding unit 10 is, for example, a loader, which serves to transport a plurality of manually set racks to the car. The preceding rack transport mechanism 12 is provided on the upper surface of the preceding unit 10 so as to extend between the opposite ends thereof in the transport direction.

Figure 4:
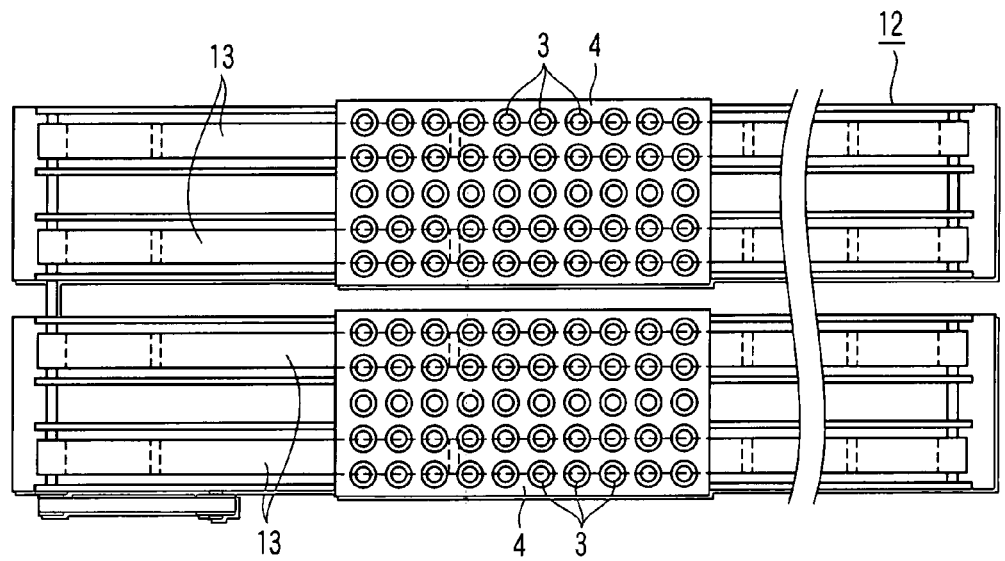
FIG. 4 is a plan view showing a preceding rack transport mechanism according to the first embodiment.
Figure 5:
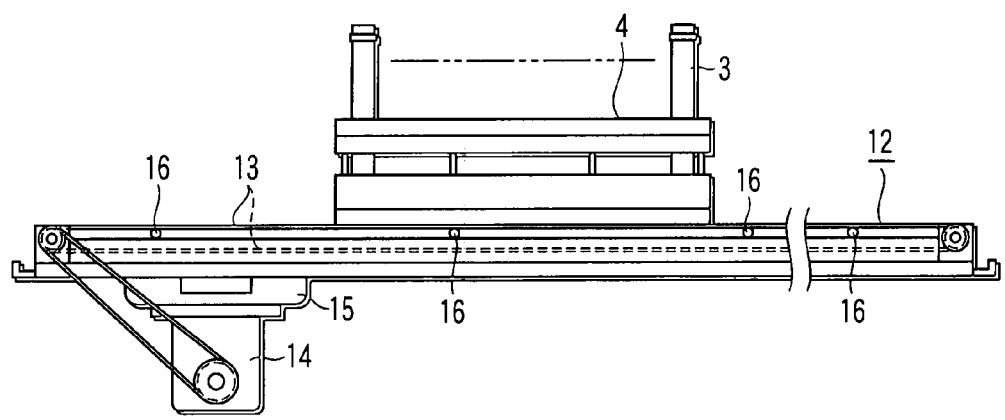
FIG. 5 is a side view showing the preceding rack transport mechanism.

As shown in FIGS. 4 and 5, the preceding rack transport mechanism 12 comprises belt conveyors 13 in a plurality of (four in FIG. 4) columns, a feed mechanism 15, rotatable rollers 16, etc. The columns, as a whole, have a predetermined width large enough to carry the racks 4 thereon. The feed mechanism 15 has a motor 14 or the like that drives the juxtaposed belt conveyors 13 for feed motion at a predetermined speed. The rollers 16 support the belt conveyors 13 from the back side. If the belt conveyors 13 are driven for feed motion with the racks 4 set thereon, the specimen containers 3 are transported for each rack 4. In the illustrated case, by way of example, each rack 4 lies spanning each two columns of the belt conveyors 13, and the four conveyors 13 are configured to transport the racks 4 in two columns in the transport direction.

Figure 6:
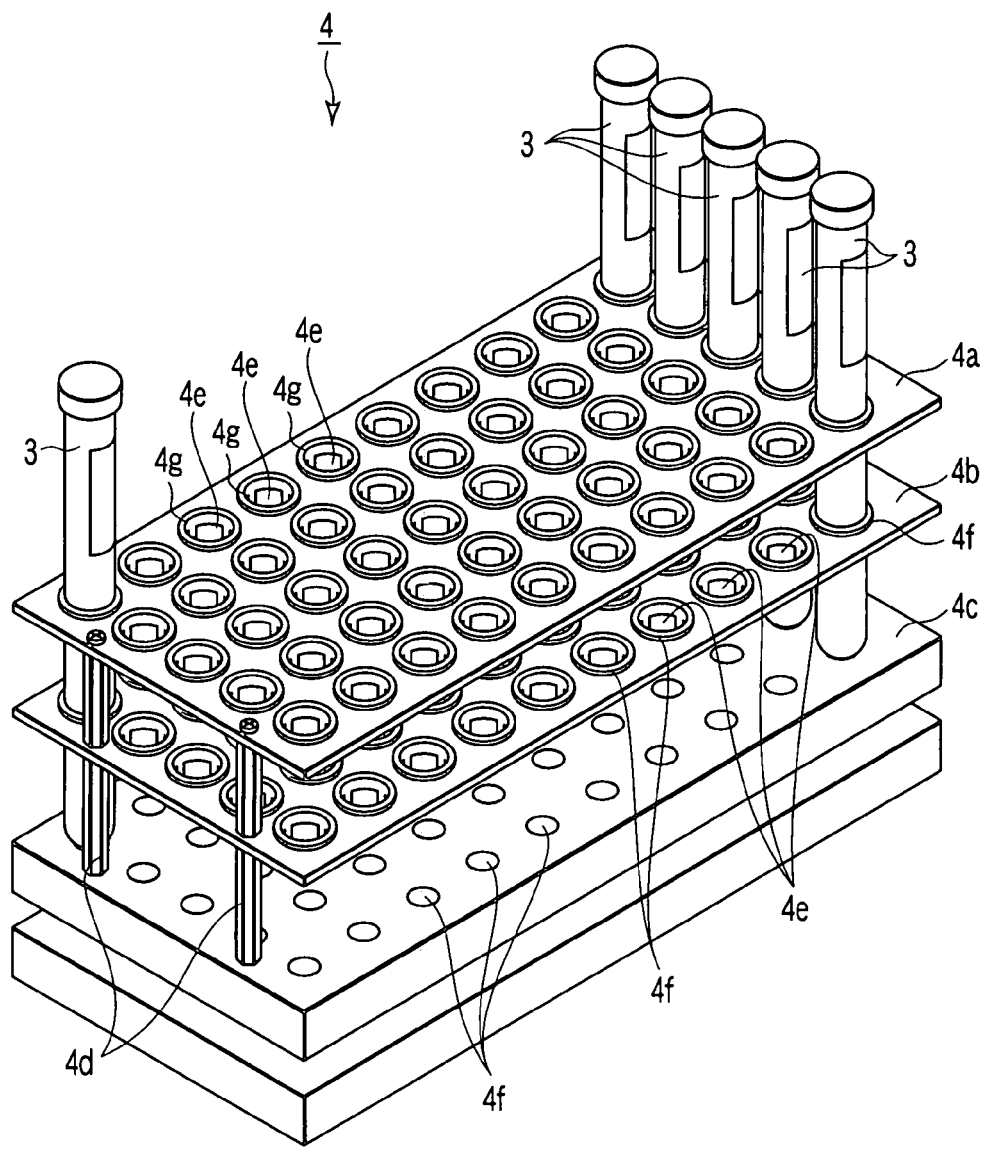
FIG. 6 is a perspective view of a rack according to the first embodiment of the invention.

As shown in FIG. 6, the rack has a function to hold a plurality of (e.g., 50 in the present embodiment) specimen containers 3, such as test tubes that contain the specimen 2, by insertion. The rack has an upper plate 4a, a middle plate 4b, and a lower plate 4c, which are spaced and opposed to one another. The upper, middle, and lower plates 4a, 4b and 4c are connected to one another by a plurality of connecting rods 4d. Each of the upper and middle plates 4a and 4b is bored with 50 container insertion holes 4e as matrix-arranged holes, 10 in each column and 5 in each row. Each insertion hole 4e is furnished with an attachment adapter 4f that can alternatively hold the specimen containers 3 of different diameters. The lower plate 4c is provided with 50 container end receiving depressions 4g that are arranged in a matrix.

As shown in FIG. 1, the guide 19 formed of a magnetic tape is laid on a floor so as to connect a downstream end position with respect to the transport direction of the preceding unit 10 and an upstream end position with respect to the transport direction of the succeeding unit 30.

As shown in FIGS. 1 to 3, a car rack transport mechanism 22 is located on the upper surface of the car 20. The transport mechanism 22, like the preceding rack transport mechanism 12, comprises belt conveyors 13 in four columns, a feed mechanism 15 having a motor 14, rollers 16, etc. The car rack transport mechanism 22 is provided with belt conveyors 23 having a predetermined length such that each two of them can carry thereon two or three racks 4 side by side.

As shown in FIG. 3, the car 20 comprises a plurality of wheels 24 formed at its lower end, an electric motor 25, a servomotor 26, and a sensor (not shown). The motor 25 serves as a drive mechanism for driving the wheels 24. The servomotor 26 serves as a redirection mechanism that can rock a wheel support fork around a vertical axis, thereby redirecting the wheels 24 at right angles. The sensor detects recorded information on the guide 19 and controls the motor 25 and the servomotor 26. With this configuration, the car 20 can reciprocate along the cranked guide 19 between the downstream end position of the preceding unit 10 and the upstream end position of the succeeding unit 30.

The succeeding unit 30 is a loader unit that feeds the specimen containers 3 transported for each rack 4, one or five at a time, from the car 20 into the specimen processing unit 80.

The succeeding rack transport mechanism 32 is provided at the upstream end of the succeeding unit 30. The transport mechanism 32, like the preceding rack transport mechanism 12, comprises belt conveyors 33 in four columns, a feed mechanism 15 having a motor 14, rollers 16, etc.

Further, the succeeding holder transport mechanism 35 is provided at the downstream portion of the succeeding unit 30.

Figure 7:
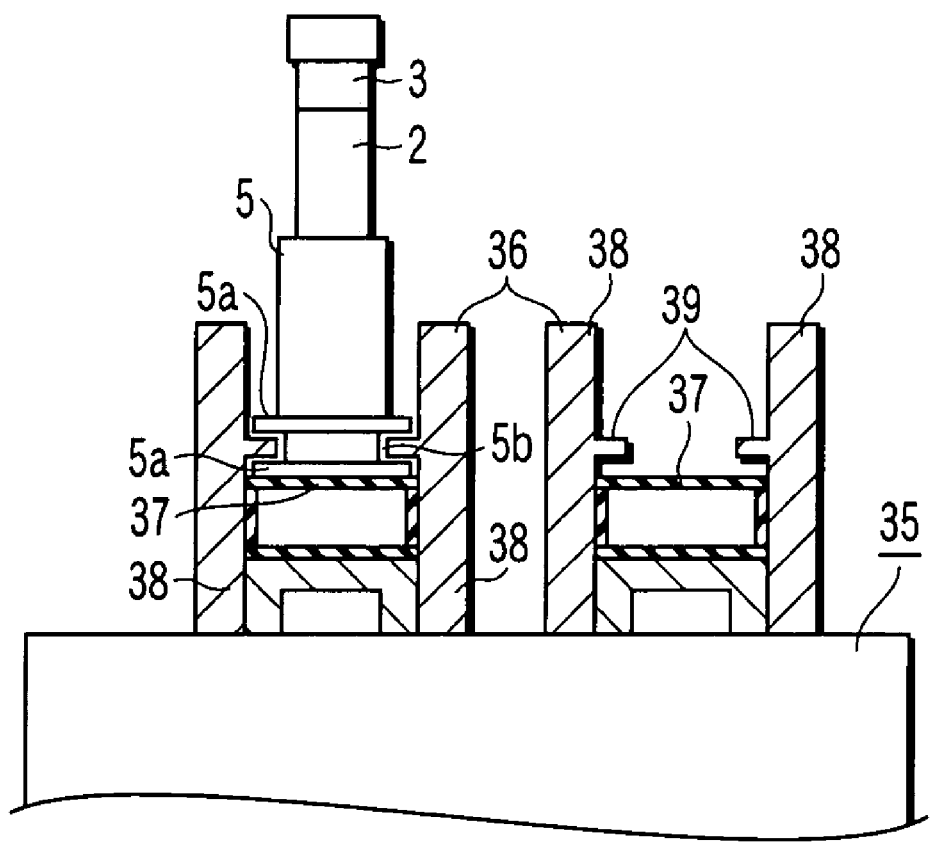
FIG. 7 is a sectional view showing a preceding holder transport mechanism according to the first embodiment.

The succeeding holder transport mechanism 35 shown in FIG. 7 has a function to transport the specimen holder 5 in which each specimen container 3, such as a test tube that contains the specimen 2, e.g., blood, is held by insertion. The specimen holder 5 has a pair of flanges 5a and an annular inter-flange groove 5b.

The succeeding holder transport mechanism 35 is provided with two transport lanes 36, belt conveyors 37, and guide rails 38 located on the opposite sides of the belt conveyors 37. Each guide rail 38 has a guide ridge 39 that engages the annular inter-flange groove 5b. As the specimen holders 5 are fed on the belt conveyors 37, the specimen containers 3 are intermittently transported at regular intervals for each specimen holder 5.

As shown in FIG. 1, the succeeding holder transport mechanism 35 is formed extending from the vicinity of the downstream end of the succeeding rack transport mechanism 32 to the downstream end of the succeeding unit 30 with respect to the transport direction. The respective transport directions of the transport mechanisms 35 and 32 are perpendicular to each other. The succeeding holder transport mechanism 35 is connected to a succeeding holder transport mechanism 35 of a specimen processing unit that is located adjacent to the downstream side of the succeeding unit 30. The specimen containers 3 are fed for each holder into the specimen processing unit by the feed motion of the transport mechanism 35.

A container hand transfer device 40 is provided extending between the downstream end of the succeeding rack transport mechanism 32 and the upstream end of the succeeding holder transport mechanism 35. The transfer device 40 comprises five open-close claws 41 (only the obverse one of which is shown in the side view of FIG. 3), a container hand 42, a cylinder 44, and a motor-operated chain mechanism 46. The claws 41 can simultaneously grasp a plurality of specimen containers 3 that adjoin one another in the direction perpendicular to the drawing plane of FIG. 3. The container hand 42 has a cylinder 43 for opening and closing the claws 41. The cylinder 44 serves to raise and lower the hand 42. The chain mechanism 46 traverses the container hand 42 and the cylinders 43 and 44 at right angles to the transport line as a slider is guided along a traverse guide 45. The container hand transfer device 40 draws out a predetermined number of specimen containers 3 successively from the racks 4 on the succeeding rack transport mechanism 32, and transfers to and inserts them into the specimen holders 5 that are delivered to a transport starting end of the transport mechanism 32.

The preceding and succeeding rack transport mechanisms 12 and 32 and the car rack transport mechanism 22, which are spaced apart from one another, are configured so that they are substantially flush with one another or that the rack transport mechanism on the downstream side is situated a little lower than the rack transport mechanisms on the upstream side. Specifically, for example, the car rack transport mechanism 22 is situated lower than the preceding rack transport mechanism 12, and the succeeding rack transport mechanism 32 is lower than the transport 22.

Further, a predetermined space is secured between the belt conveyors of the adjacent rack transport mechanisms in a preceding or succeeding mode. Specifically, the downstream end of each belt conveyor 13 of the preceding rack transport mechanism 12 with respect to the transport direction is transported downward, while the upstream end of each belt conveyor 23 of the car rack transport mechanism 22 is transported upward. The downstream end of each belt conveyor 23 is moved upward for feed motion, and the upstream end of each belt conveyor 33 of the succeeding rack transport mechanism 32 is moved downward. Thus, the belt conveyors are prevented from interfering with one another by these opposite motions, so that smooth transport is ensured.

The following is a description of steps of transporting the specimen containers 3 by the specimen transport system 1 according to the present embodiment.

When the car 20 is first located adjacent to the downstream end of the preceding unit 10, as indicated by broken line in FIG. 1, the preceding rack transport mechanism 12 and the car rack transport mechanism 22 are driven for feed motion. As these transport mechanisms are operated in this manner, the racks 4 that are previously set on the preceding unit 10 move toward the downstream end of the transport mechanism of the preceding unit 10, and run onto the upstream end portion of the car rack transport mechanism 22. As the transport mechanism 22 undergoes the feed motion, the racks 4 move downward on the transport mechanism of the car 20.

When a predetermined number of racks 4 are transferred to the car 20, the feed motion of the car rack transport mechanism 22 is stopped, whereupon the car 20 travels along the guide 19 from the preceding unit 10 toward the succeeding unit 30. Then, the succeeding mode is established in which the car 20 adjoins the succeeding unit 30, as indicated by solid line in FIG. 1.

When the feed motions of the car rack transport mechanism 22 and the succeeding rack transport mechanism 32 are started in the succeeding mode, the racks 4 on the transport mechanism 22 are transported by these feed motions. Thereupon, the racks 4 run onto the succeeding rack transport mechanism 32 and are transported toward the downstream end of the transport mechanism 32.

Then, the succeeding rack transport mechanism 32 stops, whereupon a predetermined number of specimen holders 5 in the racks 4 on the car rack transport mechanism 22 are successively transferred to the succeeding holder transport mechanism 35 by the container hand transfer device 40 over the downstream side of the transport mechanism 32. Specifically, a plurality of container hands 42 first descend, and the open-close claws 41 are closed to grasp the specimen containers 3. The hands 42 ascend in this grasping state. Further, the specimen containers 3 move to the right of FIG. 3 as they traverse along the traverse guide 45 of the cylinder 44. Finally, the container hands 42 descend, and the open-close claws 41 are opened so that the specimen holders 5 are set on the succeeding holder transport mechanism 35.

The specimen containers 3 set on the succeeding holder transport mechanism 35 are fed successively to the specimen processing units 80 and 90, dispensing or labeling units, in which the specimen is processed in a predetermined manner.

The racks 4 that are emptied by the removal of the specimen containers 3 are delivered from over a rack stage 51 of the succeeding transport mechanism and may possibly be fed to the preceding rack transport mechanism 12.

The transport system according to the present embodiment has the following effects. The construction of the specimen transport system and the processes of moving the racks can be simplified, and the time required for the rack movement can be shortened. Since the racks 4 can be transported by the conveyor feed motion only, the necessity of providing a transfer device can be obviated. Since there is no need of a step of once lifting the racks before transferring them, moreover, the transport operation is smooth, so that transport time can be shortened. Since the racks need not be grasped as they are raised, furthermore, the possibility of their being dropped or dislocated by the ascent or descent of the specimen containers 3 is reduced. Further, the car 20 is provided with the car rack transport mechanism 22 that transports the specimen containers 3 not for each specimen holder 5 but for each rack 4 that contains a large number of containers 3 therein. Therefore, the car 20 can be reduced in length in the transport direction or in size without failing to carry a large number of specimen containers 3 at a time.

Further, each rack 4 has the upper, middle, and lower plates 4a, 4b and 4c and can integrally contain a large number of specimen containers 3. Thus, the containers 3 can be held securely, and the center of gravity of the entire structure can be lowered, so that the rack 4 can be moved easily and accurately.

Figure 8:
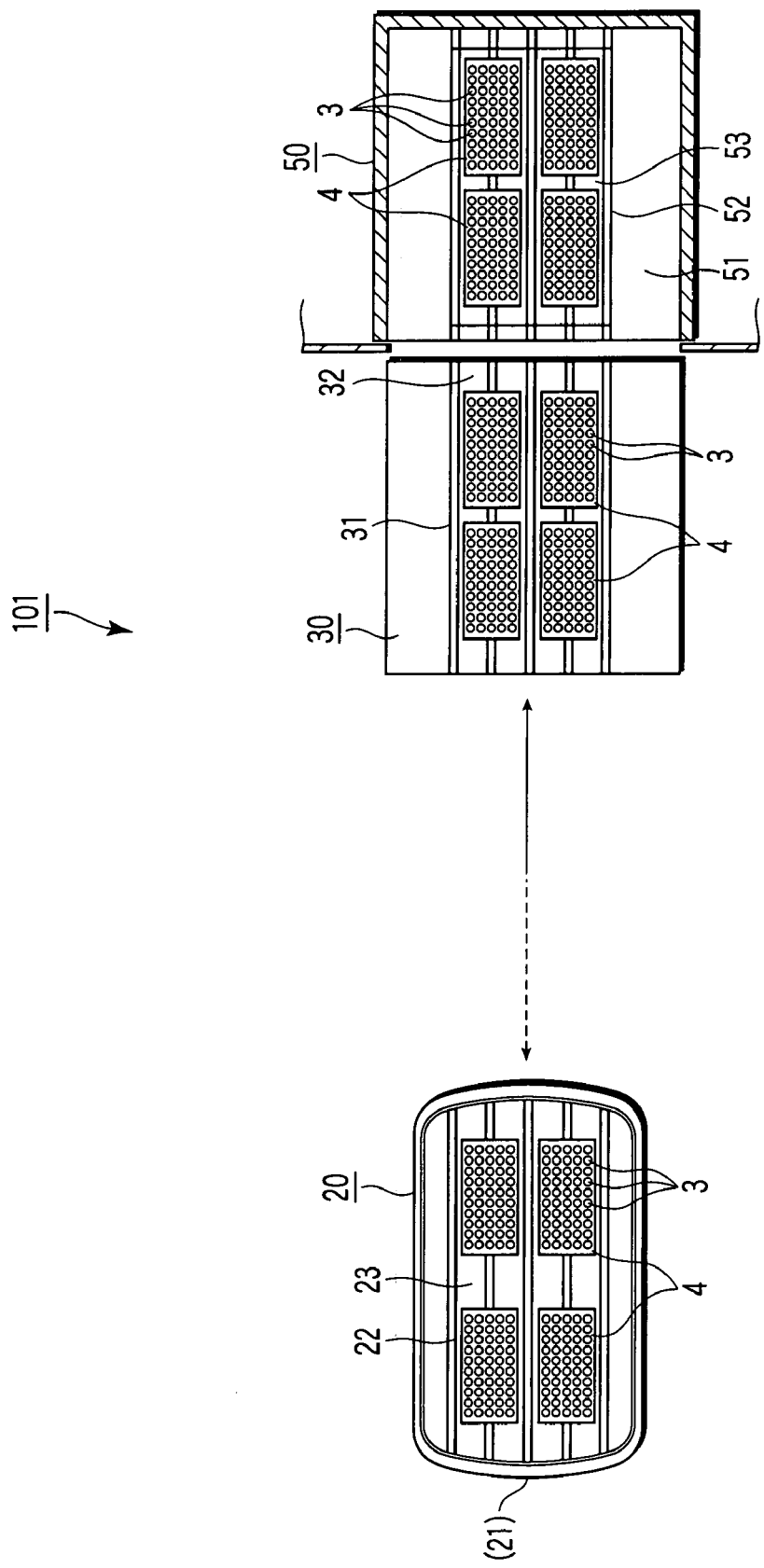
FIG. 8 is a plan view schematically showing a part of a specimen transport system according to a second embodiment of the invention.
Figure 9:
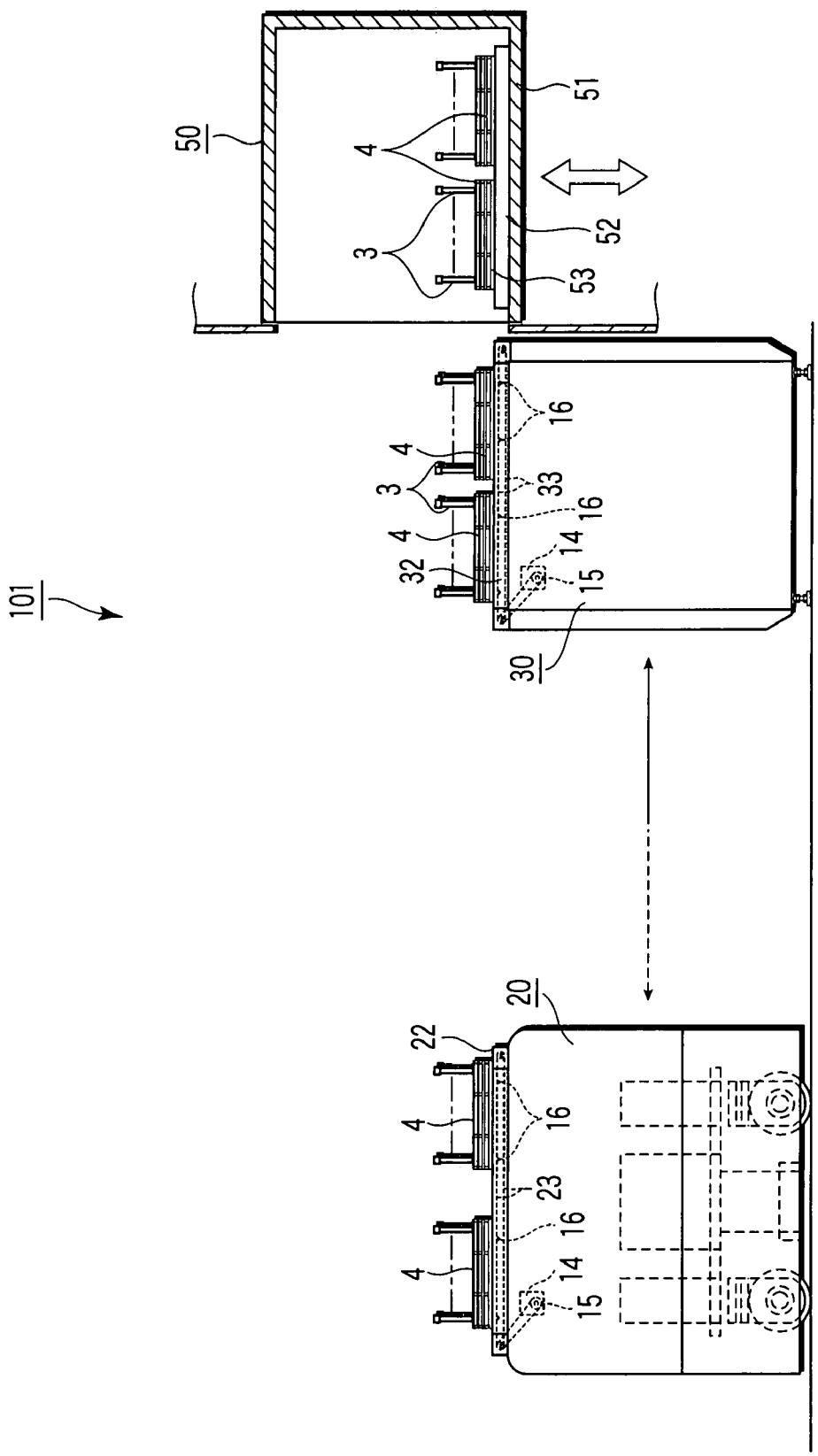
FIG. 9 is a side view schematically showing a part of the specimen transport system.

A specimen transport system 101 according to a second embodiment of the invention will now be described with reference to FIGS. 8 and 9.

In the present embodiment, a lift 50 is further located adjacent to the downstream side of a succeeding unit 30. The succeeding unit 30 of this embodiment is a specimen processing unit, such as a labeling unit, which is provided with a succeeding rack transport mechanism 32. The succeeding unit 30 is not provided with any holder transport mechanism, while the succeeding rack transport mechanism 32 is located extending between the opposite ends of the succeeding unit 30 in the transport direction.

The lift 50 is located adjacent to the downstream end of the succeeding unit 30 in the transport direction. The lift 50 is in the shape of a box having one open end face, and a liftable stage 51 is formed in the lift 50. A lift rack transport mechanism 52, which is constructed in the same manner as the aforementioned preceding rack transport mechanism, is provided on the upper surface of the stage 51. Belt conveyors 33 of the succeeding rack transport mechanism 32 are spaced from belt conveyors 53 of the lift rack transport mechanism 52 lest they touch one another.

In this specimen transport system 101, like the one according to the first embodiment, racks 4 that are moved from a car rack transport mechanism 22 to the succeeding rack transport mechanism 32 are transported from the succeeding unit 30 to the stage 51 of the lift 50 as the transport mechanism 32 and the lift rack transport mechanism 52 are operated for feed motion. If a predetermined number of racks 4 are transported into the lift 50 by the feed motion of the lift rack transport mechanism 52, the feed operation of the transport mechanisms 32 and 52 is stopped. When the lift 50 ascends or descends, specimen containers 3 vertically moved up or down.

Since the present embodiment shares other configurations and steps of transport with the foregoing first embodiment, a description thereof is omitted.

The present embodiment can provide the same effects as those of the specimen transport system 1 according to the first embodiment. Since the succeeding unit 30 is located adjacent to the lift 50, moreover, the racks 4 can be vertically moved by a simple structure.

Figure 10:
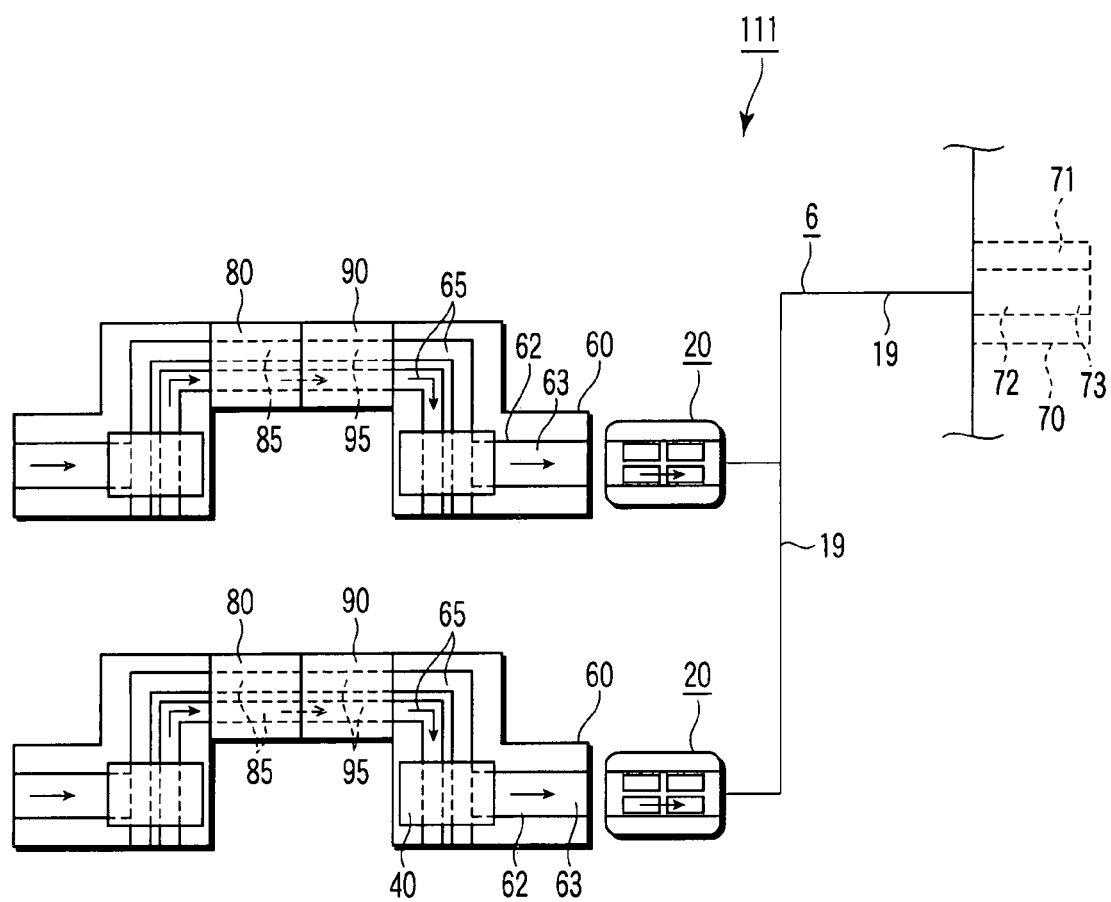
FIG. 10 is a plan view schematically showing a specimen transport system according to a third embodiment of the invention.
Figure 11:
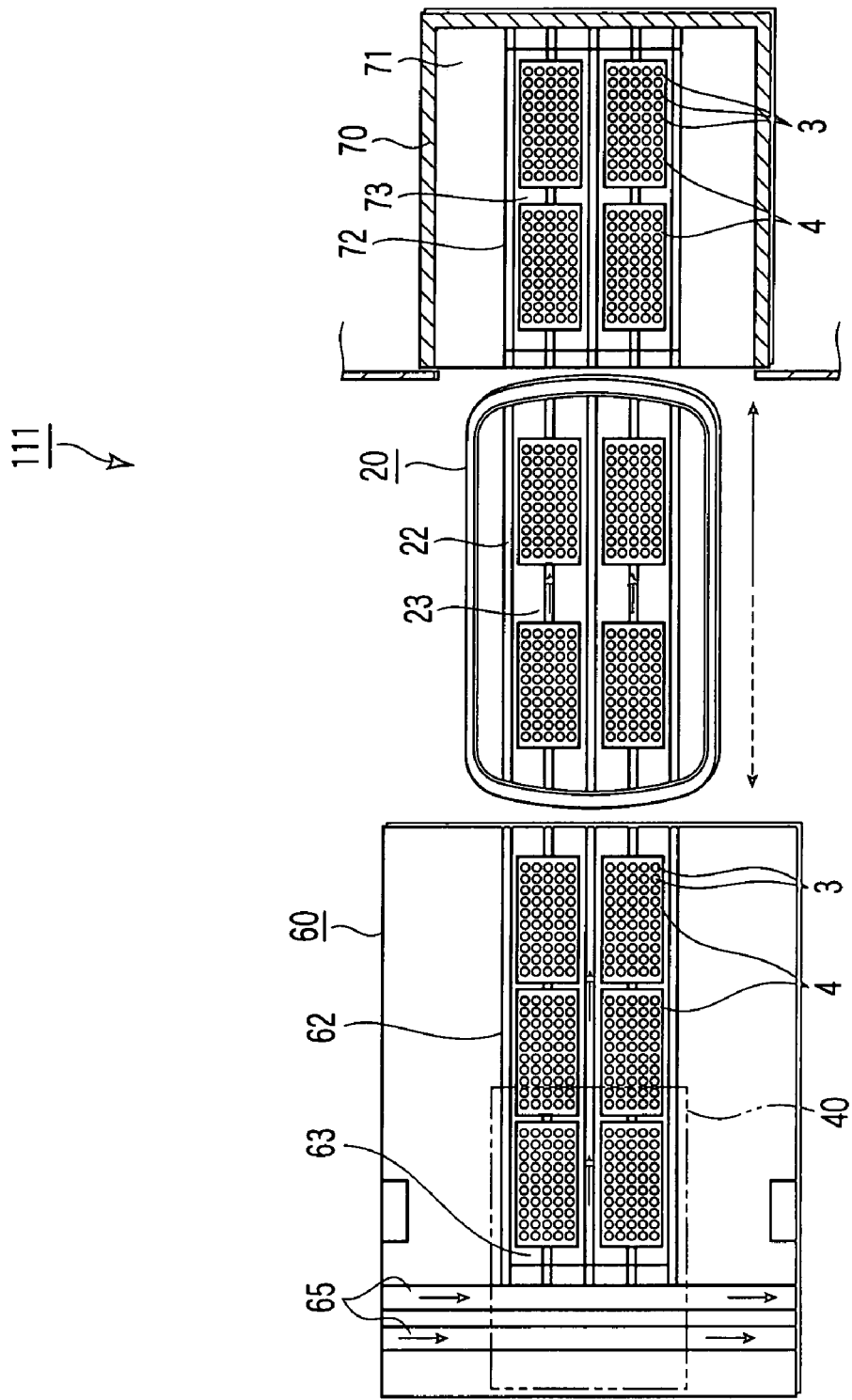
FIG. 11 is a plan view schematically showing a part of the specimen transport system of FIG. 8.
Figure 12:
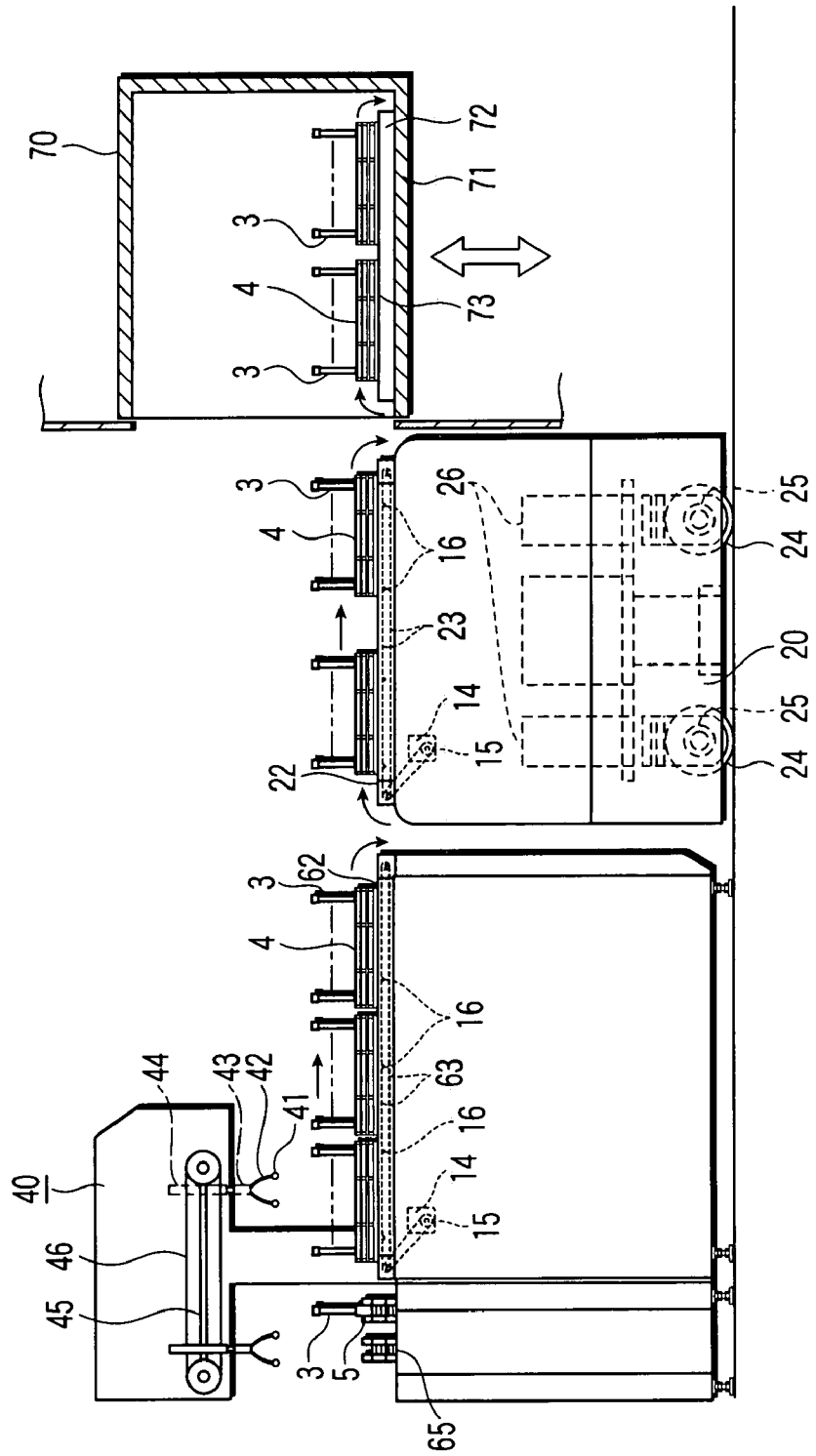
FIG. 12 is a side view schematically showing a part of the specimen transport system.

A specimen transport system 111 according to a third embodiment of the invention will now be described with reference to FIGS. 10 and 12.

In the present embodiment, a preceding unit 60 may be, for example, a dispensing unit or a labeling unit, which has a function to carry out specimen containers 3 for each rack, the containers being fed for each specimen holder 5 from various specimen processing units 80 and 90 on the upstream side in the transport direction of the preceding unit 60. A succeeding unit 70 is constructed in the same manner as the lift 50 according to the second embodiment.

The preceding unit 60 comprises a preceding holder transport mechanism 65 on the upstream side with respect to its transport direction. On the downstream side of the preceding unit 60, a preceding rack transport mechanism 62 extends from the vicinity of the downstream end of the transport mechanism 65 with respect to the transport direction to the downstream end of the preceding unit 60 with respect to the transport direction. The respective transport directions of the transport mechanisms 65 and 62 are perpendicular to each other. The preceding holder transport mechanism 65 is continuous with a holder transport mechanism 95 on the specimen processing unit 90. Further, the preceding unit 60 is furnished with a container hand transfer device 40 that is located extending between the downstream end of the transport mechanism 65 and the upstream end of the transport mechanism 62. The container hand transfer device 40 is constructed in the same manner as the container hand transfer device 40 according to the first embodiment. The transfer device 40 has a function to draw out a predetermined number of specimen containers 3 successively from the specimen holders 5 on the preceding holder transport mechanism 65 and transfer to and insert them into the preceding rack transport mechanism 62.

The following is a description of steps of transport according to this embodiment.

When the specimen holders 5 that are transported from the specimen processing unit 90 by the feed motion of the holder transport mechanism 95 are transported close to the downstream end of the preceding holder transport mechanism 65, the transport mechanism 65 is stopped by a transport line entrance stopper (not shown). In this state, the specimen containers 3 that are transported together with the specimen holders 5 are drawn out from the specimen holders 5 by the container hand transfer device 40, and a predetermined number of containers are successively transferred at a time to empty racks 4 that are supplied to and set on the preceding rack transport mechanism 62. Then, as in the first embodiment, the specimen containers 3 move for each rack 4 from the preceding rack transport mechanism 62 to a car rack transport mechanism 22 in a preceding mode such that a car 20 adjoins the preceding unit 60. Then, with the transport stopped, the car 20 travels along a guide 19 toward the succeeding unit 70 in the transport direction indicated by solid-line arrows in the drawings. In a succeeding mode such that the car 20 adjoins the succeeding unit 70, the racks 4 set on the car 20 move from over the car 20 to a stage 71 of a lift as the succeeding unit 70 as the car rack transport mechanism 22 and a succeeding rack transport mechanism 72 are operated for feed motion. When a predetermined number of racks 4 are set on the stage 71, the feed motion is stopped, and the stages ascend or descend.

The specimen holders 5 that are left in the preceding holder transport mechanism 65 by the removal of the specimen containers 3 are dropped into a holder receiving box (not shown) through a lane opening at an end of a transport line when the stopper is opened. Then, the holders 5 are supplied to another specimen processing unit or the like.

Since the present embodiment shares other configurations and steps of transport with the foregoing first embodiment, like numerals are used to designate like portions, and a description thereof is omitted.

The specimen transport system 111 can provide the same effects as those of the specimen transport systems 1 and 101 according to the first and second embodiments. Since the succeeding unit 70 is used as the lift, moreover, the system is applicable to a case where the lift and the preceding unit 60 are spaced apart from each other.

The present invention is not limited to the embodiments described above. In the description of the foregoing embodiments, a loader, unloader, dispensing unit, labeling unit, etc. are given as examples of the specimen processing units. However, some other specimen processing units may be provided in place of or in addition to those units. The other available specimen processing units include, for example, a bottle opener unit, clotting unit, etc.

According to the embodiments described above, moreover, each specimen processing unit is provided with the transport mechanism, and the specimen processing units are connected by the guide 19. Alternatively, any of the specimen processing units may be connected by a holder or rack transport mechanism.

The specimen transport systems 1, 101 and 111 of the embodiments herein may be provided with holder transport mechanisms spaced from one another and a car that is configured to travel between these transport mechanisms and provided with another holder transport mechanism, besides the aforementioned mechanisms.

It is to be understood in carrying out the present invention that the configurations, specific shapes, etc. of the components of the invention may be embodied in various modified forms without departing from the scope or spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A specimen transport system for transporting a specimen, comprising:
    a preceding section;
    a succeeding section located apart from the preceding section;
    a conveyor-type rack transport mechanism attached to each of the preceding section and the succeeding section and configured to transport a rack capable of holding a plurality of specimen containers which contain the specimen; and
    a car configured to travel between the preceding section and the succeeding section and provided with a conveyor-type rack transport mechanism configured to transport the rack capable of holding a plurality of specimen containers,
    wherein the rack is configured to be moved from the preceding section to the car by feed motions of the preceding section and the rack transport mechanism of the car in a preceding mode such that the rack is located on the rack transport mechanism of the preceding section and such that the car adjoins the preceding section, and
    wherein the rack is configured to be moved from the car to the succeeding section by feed motions of the rack transport mechanism of the car and the rack transport mechanism of the succeeding section in a succeeding mode such that the rack is located on the rack transport mechanism of the car and such that the car adjoins the succeeding section.

2. A specimen transport system according to claim 1, wherein the preceding section comprises a holder transport mechanism of a belt-conveyor type which transports the specimen for each of specimen holders which hold the specimen containers, individually, on an upstream side with respect to a transport direction thereof, the rack transport mechanism located on a downstream side with respect to the transport direction, and a container hand transfer device which successively draws out the specimen containers, a predetermined number at a time, from the holder transport mechanism and transfers the specimen containers to the rack transport mechanism.

3. A specimen transport system according to claim 1, wherein the succeeding section comprises a holder transport mechanism of a belt-conveyor type which transports the specimen for each of specimen holders which hold the specimen containers, individually, on a downstream side with respect to a transport direction thereof, the rack transport mechanism located on an upstream side with respect to the transport direction, and a container hand transfer device which successively draws out the specimen containers, a predetermined number at a time, from the rack transport mechanism and transfers the specimen containers to the holder transport mechanism.

4. A specimen transport system according to claim 1, wherein a lift having a liftable stage is located on a downstream side with respect to the transport direction of the succeeding section, the stage being provided with a conveyor-type rack transport mechanism configured to transport the rack capable of holding a plurality of specimen containers.

5. A specimen transport system according to claim 1, wherein the succeeding section is a lift having a liftable stage provided with a conveyor-type rack transport mechanism configured to transport the rack capable of holding a plurality of specimen containers.

6. A car for specimen transport comprising:
    wheels;
    a redirection mechanism configured to redirect the wheels at right angles; and
    a conveyor-type rack transport mechanism configured to transport a rack capable of holding a plurality of specimen containers which contain a specimen,
    wherein the car is configured to travel between the preceding section and the succeeding section of claim 1.

* * * * *